(12) United States Patent
Johansson

(10) Patent No.: US 7,082,326 B2
(45) Date of Patent: Jul. 25, 2006

(54) METHOD OF MAGNETIC RESONANCE IMAGING

(75) Inventor: Lars Johansson, Uppsala (SE)

(73) Assignee: Amersham Health AS, Oslo (NO)

( * ) Notice: Subject to any disclaimer, the term of this patent is extended or adjusted under 35 U.S.C. 154(b) by 187 days.

(21) Appl. No.: 10/256,397

(22) Filed: Sep. 27, 2002

(65) Prior Publication Data

US 2003/0135107 A1    Jul. 17, 2003

Related U.S. Application Data

(63) Continuation of application No. PCT/NO01/00137, filed on Mar. 30, 2001.

(60) Provisional application No. 60/210,911, filed on Jun. 12, 2000.

(30) Foreign Application Priority Data

Mar. 31, 2000    (GB) .................................... 0007872

(51) Int. Cl.
    *A61B 5/055* (2006.01)

(52) U.S. Cl. .................... 600/420; 600/410; 600/419; 424/9.323

(58) Field of Classification Search ................ 600/410, 600/419, 420; 424/9.32, 9.323, 9.36
    See application file for complete search history.

(56) References Cited

U.S. PATENT DOCUMENTS

| 5,315,997 A * | 5/1994 | Widder et al. .............. 600/420 |
| 5,855,868 A | 1/1999 | Fahlvik |
| 5,874,061 A | 2/1999 | Schmitt-Willich et al. |
| 6,073,041 A * | 6/2000 | Hu et al. .................... 600/410 |
| 6,208,140 B1 * | 3/2001 | Gebhardt et al. ........... 324/309 |
| 6,271,665 B1 * | 8/2001 | Berr et al. .................. 324/306 |

FOREIGN PATENT DOCUMENTS

| EP | WO 96 27394 | 9/1996 |
| WO | WO 88/00060 | 1/1988 |
| WO | WO 90/01295 | 2/1990 |
| WO | WO 90/01899 | 3/1990 |
| WO | WO 91/12025 | 8/1991 |
| WO | WO 91/12526 | 8/1991 |
| WO | WO 92/11037 | 7/1992 |
| WO | WO 95/05669 | 2/1995 |
| WO | WO 97/25073 | 7/1997 |
| WO | WO 99 06849 | 2/1999 |
| WO | WO 00 72037 | 11/2000 |

OTHER PUBLICATIONS

Small W C et al., "Dual Contrast Enhancement of Both T1- and T2-Weighted Sequences Using Ultrasmall Superparamagnetic Iron Oxide" Magnetic Resonance Imaging, vol. 11, No. 5, 1993, pp. 645-654.

Panting, Jonathan R., MB, MRCP, et al., "First-Pass Myocardial Perfusion Imaging and Equilibrium Signal Changes Using the Intravascular Contrast Agent NC100150 Injection" Journal of Magnetic Resonance Imaging 10:404-410 (1999).

*Henning et al. MRM 3: 823-833 (1986).

* cited by examiner

Primary Examiner—Ruth S. Smith
(74) Attorney, Agent, or Firm—Robert F. Chisholm

(57) ABSTRACT

A method of magnetic resonance (MR) imaging of blood perfusion in vascularized organs of interest, e.g. the myocardium, the kidneys, the brain, the liver wherein a contrast agent composition comprising a particulate superparamagnetic metal oxide is administered.

7 Claims, 1 Drawing Sheet

METHOD OF MAGNETIC RESONANCE IMAGING

CROSS-REFERENCE TO RELATED APPLICATION

Figure 1:
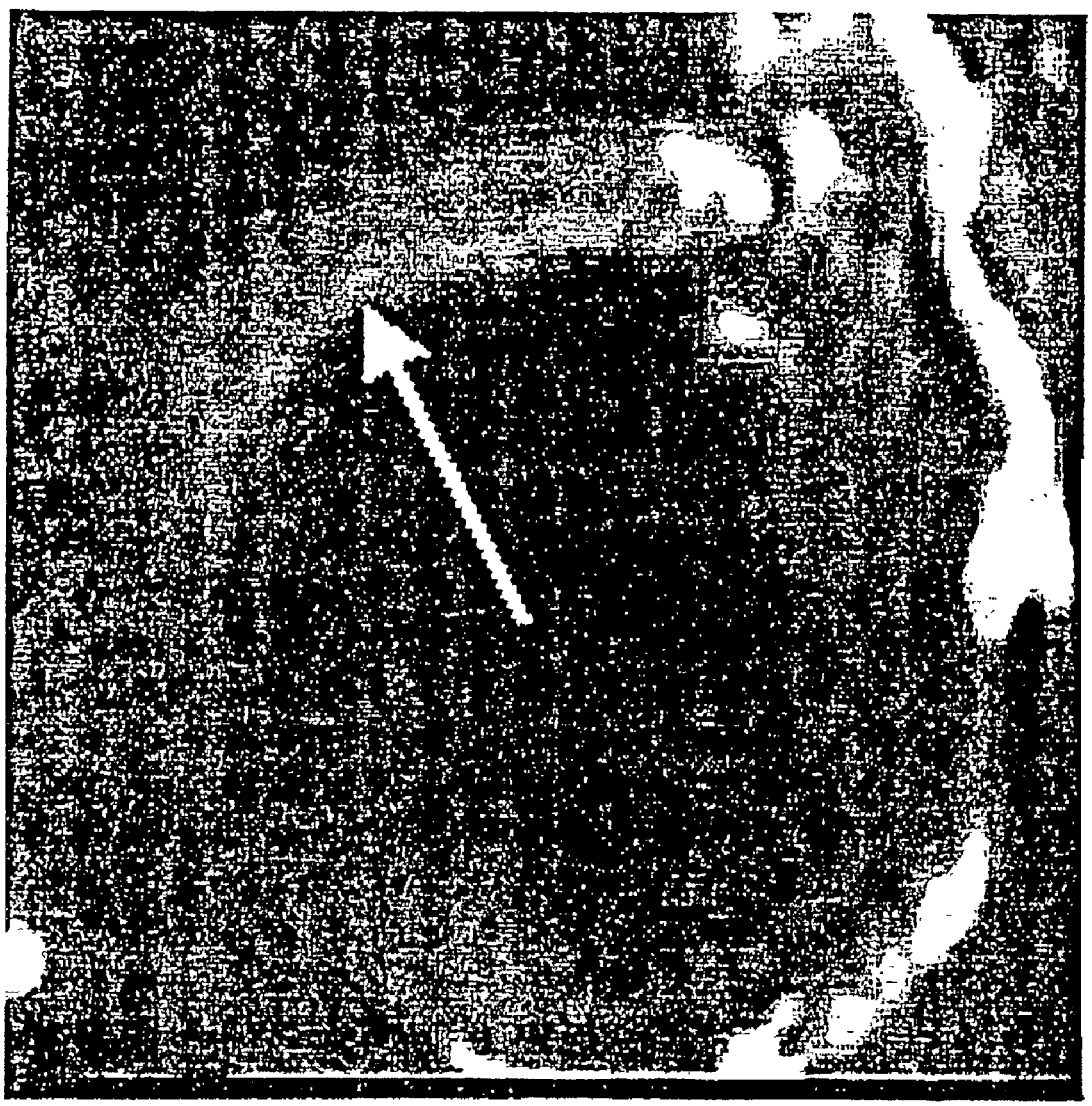

This is a continuation of International Patent Application PCT/NO01/00137, filed on Mar. 30, 2001 and published in English under Article 21(2), which claims priority of GB Patent Application No. 0007872.5, filed on Mar. 31, 2000, and U.S. 60/210,911, filed on Jun. 12, 2000.

FIELD OF THE INVENTION

This invention relates to improvements in and relating to magnetic resonance (MR) imaging of blood perfusion in vascularized organs of interest, e.g. the myocardium, the kidneys, the brain, the liver and in particular imaging of myocardial perfusion.

Viewed from one aspect the invention provides a method of first pass, contrast enhanced organ perfusion magnetic resonance imaging of a human or vascularized animal subject, wherein a MR contrast agent composition is administered into the vasculature of said subject and magnetic resonance images are generated of slices through a vascularized organ of said subject during the passage of said agent through the vasculature of said organ, and wherein said contrast agent comprises a particulate superparamagnetic metal oxide and in that said images are generated using a $T_2$-weighted Turbo (fast) spin-echo sequence and wherein said vascularized organ preferably is the myocardium, the kidneys, the brain or the liver, and more preferably the myocardium.

BACKGROUND OF THE INVENTION

In the field of cardiac imaging using magnetic resonance there has recently been great interest in the study of myocardial perfusion. Perfusion deficits revealed by such studies indicate areas of actual or potential damage to heart muscle, for example as a result of coronary infarction or total or partial arterial occlusion, and the technique can be used to monitor and assess the success of pharmacological or surgical attempts to reperfuse areas of perfusion deficit.

To date the major thrust has been in the development of first-pass myocardial perfusion imaging using $T_1$-weighted sequences and low molecular weight gadolinium chelate MR contrast agents, such as gadodiamide (Omniscan7, Nycomed Amersham) and gadopentetate (Magnevist7, Schering), agents which distribute throughout the extracellular space, i.e. within both the blood vessels and the interstitium. Generally the MR image acquisition sequences used have been very fast gradient-echo sequences or multishot echo planar imaging (EPI) sequences which rely on fast read out and a short TR in order to achieve sufficient resolution and acquire images of multiple slices through the heart in each heart beat. Such sequences usually acquire 3 or 4 slices each heart beat or 6 to 8 interleaved slices in two heart beats and the in-plane resolution is generally about 2 to 3 mm.

DETAILED DESCRIPTION OF THE INVENTION

We have now found that increased resolution can be achieved by using a particulate superparamagnetic metal oxide contrast agent, in particular an ultrasmall superparamagnetic iron oxide (USPIO) contrast agent, rather than a soluble gadolinium chelate, and by the use of a $T_2$-weighted Turbo (fast) spin-echo sequence.

Viewed from a further aspect the invention therefore provides a method of first pass, contrast enhanced myocardial perfusion magnetic resonance imaging of a human or vascularized animal (e.g. mammalian, avian or reptilian, but preferably mammalian) subject, wherein an MR contrast agent composition is administered into the vasculature of said subject and magnetic resonance images are generated of slices through the heart of said subject during the passage of said agent through the vasculature of said heart, and wherein said contrast agent comprises a particulate superparamagnetic metal oxide (preferably an USPIO) and in that said images are generated using a $T_2$-weighted Turbo (fast) spin-echo sequence.

Viewed from a yet further aspect the invention provides a method of generating MR images of a human or vascularized animal subject, previously administered with a MR contrast agent composition comprising a particulate superparamagnetic metal oxide (preferably an USPIO), which method comprises generating a first pass contrast enhanced organ perfusion MR image of slices through the vascularized organ of said subject and in that said images are generated using a $T_2$-weighted Turbo (fast) spin echo sequence. Preferably the organ is the myocardium, the kidneys, the brain or the liver, and more preferably the myocardium Viewed from a still further aspect the invention provides the use of a particulate superparamagnetic metal oxide (preferably an USPIO) for the manufacture of a MR contrast agent composition for use in a method of diagnosis involving first pass contrast enhanced organ perfusion magnetic resonance imaging of perfusion deficits in a vascularized organ using a $T_2$-weighted Turbo (fast) spin-echo sequence. Preferably the organ is the myocardium (heart), the kidneys, the brain or the liver and more preferably the organ is the myocardium (heart).

Viewed from a still further aspect the invention provides the use of a MR contrast agent composition comprising a particulate superparamagnetic metal oxide in MR imaging of a human or vascularized animal subject by generating a MR image of slices through a vascularized organ of said subject using a $T_2$-weighted Turbo (fast) spin-echo sequence following administration of said composition into the vasculature of said subject. Preferably the organ is the myocardium (heart), the kidneys, the brain or the liver and more preferably the organ is the myocardium (heart).

The methods of the invention are preferably used to generate images of at least two slices per vascularized organ cycle, preferably cardiac cycle, e.g. 2 to 10 slices/cycle, preferably 3 to 5 slices/cycle. Where the image of the heart is to be built up from images from more than one cardiac cycle, e.g. from two or less preferably three cycles, the slices from separate cycles are preferably interleaved.

Unlike the gadolinium chelates whose contrast effect in the vasculature is generally due to their $T_1$ reducing effect, superparamagnetic contrast agents, especially USPIOs, have both $T_1$ and $T_2/T_2^*$ reducing effects, the latter of which can dominate at high concentrations. Thus, since on first pass of a superparamagnetic contrast agent through the heart's vasculature the contrast agent concentration can be relatively high, the $T_2/T_2^*$ effect can be used for the first pass imaging, e.g. in a $T_2$-weighted Turbo (fast) spin echo sequence. Such a sequence is preferably used in a single shot acquisition (i.e. where an entire image rather than a single image line is read out per rf-excitation) allowing the use of pre-saturating slabs, generally in the phase-encoding direction. In this way outer volume suppression, i.e. of the extra-cardiac signal, can be achieved without unduly prolonging the image acquisition time since a smaller field of view (FOV), and hence fewer phase-encoding lines, are necessary to achieve the required image resolution. Thus the field of view for the cardiac image can be reduced significantly, e.g. to a value commensurate with the heart cross section dimension, so causing an increase in resolution. This reduction in FOV cannot be done using conventional $T_1$-weighted gradient echo imaging with gadolinium chelates since the pre-saturation pulses would need to be applied within each sequence cycle, i.e. within each TR, and would accordingly increase TR so much that it would not be possible to acquire sufficient slices within each cardiac cycle.

The superparamagnetic MR contrast agent used according to the invention may be any physiologically tolerable agent comprising superparamagnetic iron oxide (or doped iron oxide) particles. However particles which have a blood half life (measured for example in the pig) of at least 10 minutes, preferably at least 30 minutes, more preferably at least 1 hour, are especially preferred. Such particles are often referred to as blood pool contrast agents. Generally the contrast agent will be a particulate material having a particle size of 1 to 8000 nm, preferably 5 to 500 nm, more preferably 5 to 100 nm. Blood residence times for such particles can be enhanced by provision of an opsonization inhibiting coating, e.g. polyalkylene oxides (e.g. PEG), glycosaminoglycans (e.g. heparin or heparinoids, dermatan, hyaluronic acid, keratan, chondroitin, etc.). Particularly suitable as USPIO agents are dextran or carboxy-dextran-coated USPIOs, the degraded starch coated USPIOs of WO97/25073 (preferably also provided with a PEG coating), AMI 7228 and the particulate agents described in WO95/05669, WO91/12526, WO91/12025, WO90/01899, WO88/00060, WO92/11037 and WO90/01295.

The superparamagnetic agents are especially preferably members of the subclass known as ultra small superparamagnetic iron oxides (USPIO). More particularly the superparamagnetic agent is preferably a water-dispersible material comprising magnetic iron oxide particles having on their surfaces (e.g. as a coating), an optionally modified carbohydrate or polysaccharide or derivative thereof, e.g. a glucose unit containing optionally modified polysaccharide or derivative thereof, preferably an optionally modified dextran or starch or derivative thereof, for example a cleaved (e.g. oxidatively cleaved) starch or carboxylated dextran. Such iron oxide complexes preferably also comprise a further material (e.g. coating material), especially one which inhibits opsonization, e.g. a hydrophilic polymer, preferably a functionalized polyalkylene oxide, more preferably a functionalized polyethylene glycol (PEG), in particular methoxy PEG phosphate (MPP).

The iron oxide complexes preferably have a core (i.e. iron oxide particle) diameter (mode diameter) of 1 to 15 nm, more preferably 2–10 nm, especially 3–7 nm, a total diameter (mode particle size) of 1 to 100 nm, more preferably 5–50 nm, especially preferably 10–25 nm, an $r_2/r_1$ ratio at 0.47T and 40EC of less than 3, more preferably less than 2.3, still more preferably less than 2.0, especially preferably less than 1.8. The saturation magentization (Msat) at 1T is preferably 10 to 100 emu/gFe, more preferably 30–90 emu/gFe.

One such agent currently undergoing clinical trials is known as NC100150 a blood pool contrast agent coated with a starch residue and further coated with a PEG component, (Clariscan™, Nycomed Imaging AS, Oslo, Norway),e.g. disclosed in WO 97/25073 (see Ex. 12).

In the methods of the invention, the superparamagnetic contrast agent composition is preferably administered by bolus injection into the vasculature, particularly a vein, e.g. a limb vein or in the case of an animal a tail vein. The bolus is preferably administered over a period of less than 3 minutes, more preferably less than 100 seconds, still more preferably less than 60 seconds, e.g. 0.3 to 10 seconds. Contrast medium injection rates will desirably be in the range 0.01 to 10 mL/sec, especially 0.3 to 3.0 mL/sec. The bolus should desirably be as tight as possible and may be sharpened by the use of a physiological saline chaser.

In the methods of the invention, the superparamagnetic MR contrast agent is preferably administered in a dose of 0.5 to 8 mg Fe/kg bodyweight, more preferably 1 to 6 mg Fe/kg, especially 2 to 5 mg Fe/kg.

The superparamagnetic contrast agent may be formulated for use in the method of the invention with conventional pharmaceutical carriers and excipients. Typically they will be in aqueous dispersion form, e.g. at an iron content of 10 to 50 mg Fe/mL, preferably 20 to 40 mg Fe/mL. Excipients that may be present include pH modifiers, chelating agents, viscosity modifiers, osmolality modifiers, etc.

The $T_2$-weighted Turbo (fast) spin echo sequence is preferably effected with a repetition time of one cardiac cycle and a FOV which is 80 to 120% of the cardiac dimension, e.g. 20 to 150 mm, especially 50 to 100 mm. Turbo (fast) spin echo imaging is described in by Henning et al in MRM 3: 823–833 (1986). Pre-saturation slabs are preferably positioned so as to avoid signal from phase wrapping and so as to enable the small FOV values to be achieved.

All documents referred to herein are hereby incorporated by reference.

BRIEF DESCRIPTION OF THE DRAWINGS AND EXAMPLES

The invention will now be described further with reference to the following non-limiting Example and the accompanying drawings in which:

FIG. 1 is a short-axis view of a pig heart with an occluded left anterior descending coronary artery generated by first pass myocardial imaging using a $T_2$-weighted single shot Turbo (fast) spin echo sequence following iv administration of an USPIO content agent.

An aqueous suspension of an USPIO blood pool MR contrast agent prepared according to the description in Example 12 of WO97/25073 was used in this Example. The characteristics of this suspension were: [Fe]=30.2 mg Fe/mL; density 1.0589 g/mL; $r_1$=19.3 $s^{-1}nM^{-1}$; $r_2$=31.2 $s^{-1}mM^{-1}$; $r_2/r_1$=1.61 (at 20 MHz and 37EC); saturation magnetization (Msat)=84 emu/g Fe.

Example 1

In Vivo Imaging 5 mg Fe/kg bodyweight of the contrast agent composition was administered by bolus injection over 2 seconds into the ear vein of a pig (30 kg) in which the left anterior descending coronary artery had been surgically ligated.

During first pass of the contrast agent (approximately seconds after administration) images of the pig's heart were generated using a 1.5T Philips magnetic resonance imaging apparatus operating a $T_2$-weighted single shot Turbo (fast)

spin echo sequence with TE at 200 ms and a FOV limited to 80 mm using pre-saturation slabs applied in the phase encoding direction outside the FOV. One slice image obtained in this way is shown in FIG. 1 of the accompanying drawings. The area of the myocardium which is non-perfused as a result of the arterial occlusion is arrowed and may clearly be seen in the image.

The invention claimed is:

1. A method of first pass, contrast enhanced organ perfusion magnetic resonance imaging of a human or vascularized animal subject, comprising administering a MR contrast agent composition comprising a particulate superparamagnetic metal oxide into the vasculature of said subject and generating magnetic resonance images of slices through a vascularized organ of said subject during the passage of said agent through the vasculature of said organ, wherein pre-saturation slabs in the phase encoding direction and a $T_2$-weighted single shot Turbo (fast) spin-echo sequence are used to generate said images.

2. The method as claimed in claim 1 wherein said vascularized organ is the myocardium, the kidneys, the brain or the liver.

3. The method as claimed in claim 1 wherein said vascularized organ is the myocardium.

4. The method according to claim 1 wherein said superparamagnetic metal oxide is a superparamagnetic iron oxide.

5. The method as claimed in claim 4 wherein said superparamagnetic iron oxide is an ultra small superparamagnetic iron oxide (USPIO).

6. The method as claimed in claim 5 wherein said ultra small superparamagnetic iron oxide (USIPO) having on its surface an optionally modified carbohydrate or polysaccharide or derivative thereof.

7. The method as claimed in claim 1 wherein said MR contrast agent composition is administered by bolus injection over a period of less than 3 minutes.

* * * * *